(12) United States Patent
Horn

(10) Patent No.: US 8,889,112 B2
(45) Date of Patent: Nov. 18, 2014

(54) OPHTHALMIC FORMULATIONS INCLUDING SELECTIVE ALPHA 1 ANTAGONISTS

(75) Inventor: Gerald Horn, Deerfield, IL (US)

(73) Assignee: Ocularis Pharma, LLC, North Riverside, IL (US)

(*) Notice: Subject to any disclaimer, the term of this patent is extended or adjusted under 35 U.S.C. 154(b) by 1331 days.

(21) Appl. No.: 10/867,144

(22) Filed: Jun. 14, 2004

(65) Prior Publication Data

US 2005/0080056 A1 Apr. 14, 2005

Related U.S. Application Data

(63) Continuation-in-part of application No. 09/854,414, filed on May 10, 2001, which is a continuation-in-part of application No. 09/710,758, filed on Nov. 8, 2000, now Pat. No. 6,420,407, which is a continuation-in-part of application No. 09/705,526, filed on Nov. 3, 2000, now abandoned, which is a continuation-in-part of application No. 09/675,988, filed on Sep. 29, 2000, now Pat. No. 6,730,065, which is a continuation-in-part of application No. 09/662,945, filed on Sep. 15, 2000, now Pat. No. 6,291,498.

(60) Provisional application No. 60/154,893, filed on Sep. 20, 1999, provisional application No. 60/154,033, filed on Sep. 16, 1999.

(51) Int. Cl.
| | | |
|---|---|---|
| A61K 31/74 | (2006.01) | |
| A61K 31/517 | (2006.01) | |
| A61K 31/4164 | (2006.01) | |
| A61K 31/4745 | (2006.01) | |
| A61K 31/496 | (2006.01) | |
| A61K 31/66 | (2006.01) | |
| A61K 31/00 | (2006.01) | |
| A61K 31/138 | (2006.01) | |
| A61K 31/417 | (2006.01) | |
| A61K 31/475 | (2006.01) | |
| A61K 31/4168 | (2006.01) | |
| A61K 31/551 | (2006.01) | |
| A61K 45/06 | (2006.01) | |
| A61K 31/166 | (2006.01) | |
| A61K 31/18 | (2006.01) | |

(52) U.S. Cl.
CPC .......... *A61K 45/06* (2013.01); *A61K 31/517* (2013.01); *A61K 31/4164* (2013.01); *A61K 31/4745* (2013.01); *A61K 31/496* (2013.01); *A61K 31/66* (2013.01); *A61K 31/00* (2013.01); *A61K 31/138* (2013.01); *A61K 31/417* (2013.01); *A61K 31/475* (2013.01); *A61K 31/4168* (2013.01); *A61K 31/551* (2013.01); *A61K 31/166* (2013.01); *A61K 31/18* (2013.01)
USPC ........................................................ 424/78.04

(58) Field of Classification Search
USPC ........................................................ 424/78.04
See application file for complete search history.

(56) References Cited

U.S. PATENT DOCUMENTS 3,556,099 A * 1/1971 Knight et al. .................. 604/232
4,443,441 A   4/1984 Galin (Continued)

FOREIGN PATENT DOCUMENTS

| CA | 2 569 468 | 12/2013 |
|---|---|---|
| JP | 07-330726 | 12/1995 |

(Continued)

OTHER PUBLICATIONS

Moriyama et al (European Journal of Pharmacology 337(1997) 39-42).*

(Continued)

*Primary Examiner* — Benjamin Packard
(74) *Attorney, Agent, or Firm* — K&L Gates LLP

(57) ABSTRACT

Ophthalmic formulations are provided. The ophthalmic formulations include one or more active agents that act to optimize pupil light reflex while minimizing, or effectively eliminating, any undesired eye redness in response to application thereof. The active agents include, for example, alpha 1 antagonists, such as alpha 1a selective antagonists.

44 Claims, 1 Drawing Sheet

(56) References Cited

U.S. PATENT DOCUMENTS

| | | | |
|---|---|---|---|
| 4,515,295 A | | 5/1985 | Dougherty |
| 4,629,456 A | | 12/1986 | Edwards |
| 4,834,727 A | | 5/1989 | Cope |
| 4,906,613 A | | 3/1990 | Watkins |
| 5,059,188 A | | 10/1991 | Goddard |
| 5,134,124 A | | 7/1992 | Nisato et al. |
| 5,252,595 A | | 10/1993 | Gluchowski |
| 5,322,704 A | * | 6/1994 | Gaonkar ............... 426/601 |
| 5,478,858 A | * | 12/1995 | Cupps et al. ............. 514/394 |
| 5,514,118 A | | 5/1996 | Kummer et al. |
| 5,584,823 A | | 12/1996 | Valberg |
| 5,591,426 A | | 1/1997 | Dabrowski et al. |
| 5,627,611 A | | 5/1997 | Scheiner |
| 5,792,767 A | | 8/1998 | Meyer et al. |
| 5,891,882 A | | 4/1999 | Meyer et al. |
| 5,891,913 A | | 4/1999 | Sallmann et al. |
| 5,895,645 A | | 4/1999 | Dabrowski et al. |
| 5,895,654 A | | 4/1999 | Hartford |
| 6,046,207 A | | 4/2000 | Meyer et al. |
| 6,291,498 B1 | | 9/2001 | Horn |
| 6,319,464 B1 | | 11/2001 | Asgharian |
| 6,420,407 B1 | | 7/2002 | Horn |
| 6,515,006 B2 | | 2/2003 | Horn |
| 6,730,065 B1 | | 5/2004 | Horn |
| 2002/0082288 A1 | | 6/2002 | Horn |
| 2002/0187986 A1 | | 12/2002 | Horn |
| 2005/0080056 A1 | | 4/2005 | Horn |
| 2005/0220831 A1 | * | 10/2005 | Jorsal ............... 424/401 |
| 2006/0211753 A1 | | 9/2006 | Horn |

FOREIGN PATENT DOCUMENTS

| | | |
|---|---|---|
| WO | 99-15202 | 1/1999 |
| WO | 2001-19364 A1 | 3/2001 |
| WO | 2004-017960 A1 | 3/2004 |

OTHER PUBLICATIONS

Ball et al (J. Vet. Pharmacol. Therap. 20 (1997) 100-104).*
Wellman et al (Pharmacology Biochemistry and Behavior, vol. 57, Nos. 1/2, pp. 281-284, 1997).*
U.S. Appl. No. 09/675,988, filed Sep. 29, 2000, Horn.
U.S. Appl. No. 09/705,526, filed Sep. 29, 2000, Horn.
Bedford Laboratories, *Phentolamine Mesylate for Injection, USP*, May 1999.
Van Alphen, G., *The adrenergic receptors of the intraocular muscles of the human eye*, Investigative Ophthalmology, Jun. 1976, vol. 15, No. 6, pp. 502-505.
Yoshitomi, T., et al., *Adrenergic Excitatory and Cholinergic Inhibitory Innervations in the Human Iris Dilator*, Exp. Eye Res. 1998, vol. 40, pp. 453-459.
Lee, Y.C., et al., *Influence of dioptric correction and pupil size on visual function*, J. Cataract Refract. Surg., 2003, vol. 29, pp. 769-777.
Thordsen, J.E., et al., *Effect of Brimonidine Tartrate Ophthalmic Solution 0.15% on Pupil Diameter in Normal Eye*, Apr. 25, 2003.
Padma-Nathan, H., et al., *Long-term safety and efficacy of oral phentolamine mesylate (Vasomar) in men with mild to moderate erectile dysfunction*, International Journal of Impotence Research, Aug. 2002, vol. 14, No. 4., pp. 266-270.
Heller, P.H., et al., *Autonomic components of the human pupillary light reflex*, Investigate Ophthalmology & Visual Science, Vo. 31, No. 1, Jan. 1990, pp. 156-162.
King, V.M., *Effects of mydriatics and a miotic on ocular discomfort and pupil responses*, Journal of the American Optometric Association, vol. 47, No. 7, Jul. 1976, pp. 937-942.
Hill, C.E., et al., *Specificity of Innervation of Iris Musculature by Sympathetic Nerve Fibres in Tissue Culture*, Pflügers Arch., 1976, vol. 361, pp. 127-134.
Lograno, M.D., et al., *Receptor-responses in fresh human ciliary muscle*, Br. J. Pharmac., 1986, vol. 87, pp. 379-385.
Zetterström, C., et al., *Pharmacological Characterization of Human Ciliary Muscle Adrenoceptors in Vitro*, Exp. Eye Res., 1988, vol. 46, pp. 421-430.

Takayanagi, I., et al., $\alpha_{-1B}$—*Adrenoceptor Mechanisms in Rabbit Iris Dilator*, Japan. J. Pharmacol., 1992, vol. 59, pp. 301-305.
Ishikawa, H., et al., *Comparison of post-junctional α-adrenoceptors in iris dilator muscle of humans, and albino and pigmented rabbits*, Naun. Schmed., 1996, vol. 354, pp. 165-172.
Yu, Y., et al., $\alpha_{-1A}$-*Adrenoceptors Mediate Sympathetically Evoked Pupillary Dilation in Rats*, JPET, Feb. 2002, vol. 300, Issue 2, pp. 521-525.
Benson, G.S., et al., *Is Phentolamine Stable in Solution with Papaverine*, The Journal of Urology, Nov. 1988, Vo. 140, pp. 970-971.
Hadzija, B.W., et al., *Physicochemical Stability of Papaverine Hydrochloride-phentolamine Mesylate Mixtures used for Intracavernous Injection: A Preliminary Evaluation*, The Journal of Urology, Jan. 1988, vol. 140, pp. 64-65.
Soli, M., et al., *Vasoactive Cocktails for Erectile Dysfunction: Chemical Stability of PGE1, Papaverine and Phentolamine*, The Journal of Urology, Aug. 1998, vol. 160, pp. 551-555.
Tu, Y.H., et al., *Stability of papaverine hydrochloride and phentolamine mesylate in injectable mixtures*, American Journal of Hospital Pharmacy, vol. 44, Nov. 1987, pp. 2524-2527.
Wang, D.P., et al., *Degradation Kinetics of Phentolamine Hydrochloride in Solution*, Journal of Pharmaceutical Sciences, Nov. 1988, vol. 77, No. 11, pp. 972-976.
H. Uusitalo, *An acute ocular inflammatory reaction induced by intravitreal bovine serum albumin in presensitized rabbits: the effect of phentolamine*, Acta. Ophthalmol. (Copenh), Aug. 1994, vol. 63, No. 4, pp. 636-642.
Nielsen, C.B., et al., *Effect of α- and β-receptor active drugs on corneal thickness*, Acta Ophtahal., 1985, vol. 63, pp. 351-354.
Goodman & Gillman's *The Pharmacological Basis of Therapeutics*, (Ninth Edition) at pp. 225-232.
Chou B., et al., *The Role of Pupil Size in Refractive Surgery*, Feb. 2001, www.refractivesource.com/doctors/clinical_pearls/role_pupil.htm.
Refractive Surgery, Jun. 22, 2000, http://www/eyecarest.com/refractive_surgery.html.
Canadian Office Action for corresponding 2,569,468 issued on Oct. 1, 2012.
Japanese Office Action for Japanese Application No. P2011-237754, dated Apr. 30, 2014.
Japanese Office Action for corresponding JP2011-237754 issued on Aug. 20, 2013.
H. Uusitalo, *The effect of autonomic receptor blockers on the ocular response to topical chemical irritation*, Acta. Physiol. Scand., May 1984, vol. 121, No. 1, pp. 1-8.
Davies, NM: *Biopharmaceutical considerations in topical ocular drug delivery*, Clin. Exp. Pharmacol. physiol., 2000, vol. 27, No. 7, pp. 558-562.
Alster, Y., et al., *Dapiprazole for patients with night haloes after excimer keratectomy*, Graefe's Arch. Clin. Exp. Ophthalmol., 1996, vol. 234, pp. S139-S141.
McDonald II, J.E., et al., *Effect of brimonidine tartrate ophthalmic solution 0.2% on pupil size in normal eyes under different luminance conditions*, J. Cataract Refract. Surg., Apr. 2001, vol. 27, pp. 560-564.
O'Brart, D.P.S., et al., *Disturbances in night vision after excimer laser photorefractive keratectomy*, Eve, 1994, vol. 8, pp. 46-51.
Fan-Paul, N.I., et al., *Night Vision Disturbances After Corneal Refractive Surgery*, Survey of Ophthalmology, Nov.-Dec. 2002, vol. 47, No. 6, pp. 533-546.
Connor, C.G., et al., *The clinical efficacy of Rēv-Eyes™ in reversing the effects of pupillary dilation*, Journal of the American Optometric Association, J. Am. Optom. Assoc., 1993, vol. 64, pp. 634-636.
O'Brart, D.P.S., et al., *Night vision after excimer laser photorefractive keratectomy: haze and halos*, European Journal of Ophthalmology, 1994, vol. 4, No. 1, pp. 43-51.
Nielsen, C.B., et al., *Effect of 60 - and β-receptor active drugs on corneal thickness*, Acta Ophtahal., 1985, vol. 63, pp. 351-354.
Goodman & Gillman's *The Pharmacological Basis of Therapeutics*, (Ninth Edition) at pp. 225-232, 1996.

(56) References Cited

OTHER PUBLICATIONS

Nicola Iuglio, MD, *Ocular Effects of Topical Application of Dapiprazole in Man*, Glaucoma, 1984, vol. 6, pp. 110-116.

European Office Action for European Application No. 05 757 147.3, dated Oct. 7, 2010.

Nuyts et al., "Intraocular irrigating solutions: a comparison of Hartmann's lactated Ringer's solution, BSS and BSS Plus," Graefe's Arch Clin Exp Ophthalmol (1995) 233:655-661.

Office Action for U.S. Appl. No. 09/854,414, dated Nov. 6, 2013.

Office Action for U.S. Appl. No. 11/381,011, dated Dec. 13, 2013.

Taylor et al., The Circulatory Effects of Intravenous Phentolamine in Man, Circulation, vol. XXXI, May 1965, pp. 741-754.

Yu et al., "Non-inferiority of silodosin to tamsulosin in treating patients with lower urinary tract symptoms (LUTS) associated with benign prostatic hyperplasia (BPH)." BJU Int. Dec. 2011; 108(11): 1843-8 (abstract).

\* cited by examiner

OPHTHALMIC FORMULATIONS INCLUDING SELECTIVE ALPHA 1 ANTAGONISTS

CROSS REFERENCES TO RELATED APPLICATIONS

The present application is a continuation-in-part of U.S. application Ser. No. 09/854,414 filed on May 10, 2001; which is a continuation-in-part of earlier filed U.S. application Ser. No. 09/710,758 filed Nov. 8, 2000 that issued as U.S. Pat. No. 6,420,407 on Jul. 16, 2002; which is a continuation-in-part of earlier filed U.S. application Ser. No. 09/705,526 filed Nov. 3, 2000 now abandoned; which is a continuation-in-part of earlier filed U.S. application Ser. No. 09/675,988 filed Sep. 29, 2000; that issused as U.S. Pat. No. 6,730,065 on May. 4, 2004; which is a continuation-in-part of earlier filed U.S. application Ser. No. 09/662,945 filed Sep. 15, 2000 that issued as U.S. Pat. No. 6,291,498 on Sep. 18,2001 which claims priority to provisional patent applications Ser. Nos. 60/154,893 filed Sep. 20, 1999 and 60/154,033 filed Sep. 16, 1999; all of which applications are incorporated herein by reference and to which application is claimed priority under the appropriate section of Title 35 of the U.S.C.

BACKGROUND OF THE INVENTION

The present invention relates to compositions formulated for administration to an eye. More specifically, the present invention relates to compositions formulated and administered to a human eye to improve vision, such as to reduce excessive pupil dilation in a reduced light including absent lighting conditions.

While it is generally known that pupil size varies in its diameter in a reduced light between individuals from 3 mm to 9 mm, little attention has been paid to the effect of this difference on vision, such as on night vision, vision in dim light and the like. However, individuals with large pupils suffer from much more light scatter, glare, halo, and related aberrant focus of light rays that can make function under certain conditions of lighting very difficult as disclosed in U.S. Pat. No. 6,515,006. This is due to the fact that the eye must focus through as much as nine times more corneal surface area in dim light conditions as compared to bright light conditions.

As the corneal curvature becomes increasingly imperfect as a function of distance from the corneal center, a greater degree of undesirable light scattering occurs the larger the corneal surface area is through which light is allowed to focus. This is particularly relevant to night vision and vision in any dimly lit environment, where the ideal surface area required for sufficient light entry is far exceeded due to genetic factors related to the light reflex common to many individuals. It therefore is desirable to minimize this excessive pupil response to a reduced light in such individuals.

The pupillary dilation that occurs in a reduced light including complete darkness allows increased light to enter the eye. However, a pupil size of about 3 mm to about 4 mm is the maximum size needed for this purpose, allowing 9 to 16 times more light to enter as compared to a 1 mm pupil in bright illumination. The mean pupil size in several studies of normal populations has been shown to be much larger, namely, about 6.1 mm. More recent studies using recently available technology for mapping optical imperfections known as higher order aberrations (HOA's, such as spherical aberration, coma, secondary astigmatism, trefoil, and the like) demonstrate a strong correlation between the increase in pupil size in darkness above 4 mm and the degree of HOA's to which the eye is exposed.

Further, individuals with increased optical refractive error, individuals with only partial correction of their refractive error, such as soft contact lens wearers with uncorrected astigmatism, individuals with excessive higher order aberrations, and individuals with previous refractive surgery with optical zones much smaller than their mesopic or scotopic pupil, refractive surgery with other induced higher order aberrations, and the like have still greater reduction in their quality of vision and/or contrast sensitivity (e.g., visual acuity in a reduced light), and an even more dramatic need for a reduced pupil light reflex response to reduced illumination. Laser vision correction in particular has added new quality of vision difficulties for many of these individuals. Exposing the retina to light focusing from as much as nine times more surface area than is necessary essentially magnifies every variation in curvature from the ideal. For example, a normal healthy population of individuals selected only for nearsightedness and/or astigmatism demonstrates over a 20% incidence of difficulty with night vision and night driving, as documented by the FDA for approval of recent laser vision correction machines.

In general, direct acting miotic agents, such as pilocarpine, have been used in an effort to decrease pupil size. However, pilocarpine causes brow ache, ciliary muscle contraction and pseudo myopia, excessive dimness when first applied since the pupil size is usually reduced to less than 2 mm, and redness. Its miotic effect is believed to last only a few hours, and it has a known, though remote, risk of retinal detachment. This is probably related to the pull on the retina from stimulated ciliary muscle contraction. In addition to pilocarpine, the use of certain sulfamoyl-substituted phenethylamine derivatives to reverse drug-induced mydriasis (e.g., dilation of the pupil caused by the administration of a drug) are disclosed in U.S. Pat. No. 5,288,759.

In general, alpha 1 antagonists are known to have propensity to reverse pupillary dilation with cyloplegic agents, and hence it might be inferred reduce the pupil light reflex. But, at the same time, the alpha 1 antagonists are by their intrinsic nature known to cause dilation of conjunctival and/or scleral vessels. This can cause undesirable redness to the eye. Of these, phentolamine has been demonstrated to have one of the best profiles with respect to pupil light reflex reduction and minimal induction of vascular dilation, and thus is useful for the purpose of reducing the pupil light reflex when applied as in topical eye medication disclosed in U.S. Pat. No. 6,515,006.

Another medication used to reverse pupillary dilation and studied for its effect on pupil size is dapiprazole, an alpha 1 adrenergic receptor blocking agent. Dapiprazole is 5,6,7,8 tetrahydro-3-[2-(4-o,tolyl-1-piperazinyl)ethyl]-8-triazolo[4,3-a]pyridine hydrochloride. In general, it is available in a 0.5% solution to partially counteract, or reverse, the dilation effect of phenylephrine, an adrenergic dilating agent, and the dilating and accommodation loss caused by tropicamide. However, dapiprozole is known to produce substantial increased redness and conjunctival chemosis (e.g., swelling) upon instillation. Further, it has been demonstrated that dapiprazole is not as effective with respect to reducing pupil size in dim light in clinical application as compared to, for example, phentolamine and phenoxybenzamine as disclosed in U.S. Pat. No. 6,515,006 when used topically for this purpose. Because of its side effects the commercial use of dapiprazole is indicated for sporadic use, such as the reversal of iatrogenic mydriasis, and not for repeat, regular, or chronic use.

In general, the receptors that mediate pupil dilation are located within the smooth muscle of the iris and are commonly referred to as adrenergic receptors. The adrenergic receptors can be further classified as alpha 1 or alpha 2 receptors. In the iris dilator muscle, adrenergic receptors that mediate pupil dilation are alpha 1 receptors. This classification can be further subdivided into alpha 1 receptor types specific to smooth muscle (which can vary for different organ systems), and frequently different receptor alpha 1 subclassification for vascular alpha 1 adrenergic receptors.

In the human bladder, for example, alpha 1a receptors mediate bladder contraction, while alpha 1b receptors are present in vascular tissue. Tamsulosin represents a somewhat preferential alpha 1a selective antagonist, which when administered orally reduces bladder spasm with a reduced effect on blood pressure as compared to known medications that include nonselective alpha antagonists. In addition to tamsulosin, other compounds or agents, such as KMD 3213, WB-4101, and 5-methyl urapidil, have an even greater specificity for alpha 1a selectivity. For example, KMD 3213 is being studied clinically to treat bladder spasticity due to its reduced effect on vascular tissue and lower incidence of hypotension (low blood pressure) than found with nonselective alpha 1a antagonists that have been used (such as doxazosin).

A need therefore exists to provide improved ophthalmic compositions that can effectively modulate the pupil light reflex in a reduced light to a more optimal range limit of dilation, to eliminate extraneous light and eliminate higher order aberrations in such lighting, thereby enhancing vision and to do so without inducing vascular effects in the eye, such as redness.

SUMMARY OF THE INVENTION

The present invention relates to ophthalmic formulations. In general, the ophthalmic formulations can act to reduce excessive pupil dilation, particularly in a reduced light including absent lighting. In an embodiment, the compositions include an alpha 1 antagonist. Preferably, the compositions include a sub-class of alpha 1 antagonists that includes selective alpha 1 antagonists. This class of compounds can preferentially effect iris alpha adrenergic receptors over vascular alpha adrenergic receptors. In this regard, the selective alpha 1 antagonists can effectively act to reduce the pupil light reflex of an eye in a reduced light while minimizing dilation of conjunctival and/or scleral vessels. Thus, an undesirable redness response and/or chemosis can be effectively eliminated when the selective alpha 1 antagonist is applied to the eye, such as in a topical manner. Compounds selectively antagonizing the alpha 1 iris dilator smooth muscle and not the vascular tissues of the eye are ideal for the purpose of enhancing reduced light vision.

To this end, in an embodiment, the present invention provides an ophthalmic formulation. The ophthalmic formulation includes a therapeutically effective amount of a compound that selectively effects an iris alpha adrenergic receptor over a vascular alpha adrenergic receptor to optimize a pupil diameter in a reduced light while minimizing eye redness.

In an embodiment, the compound is selective for an iris dilator smooth muscle alpha adrenergic receptor.

In an embodiment, the compound effectively reduces activity of the iris dilator smooth muscle.

In an embodiment, the compound reduces activity of the iris dilator muscle effectively without effecting an iris sphincter muscle.

In an embodiment, the compound includes an alpha 1 antagonist.

In an embodiment, the alpha 1 antagonist is selective for an alpha 1a adrenergic receptor over an alpha 1b adrenergic receptor.

In an embodiment, the alpha 1 antagonist includes sulfonamides including tamsulosin; uracils including A-131701, fiduloxasin, Ro-70-004, urapidil and 5-methyl urapidil; piperidines including 4-oxospiro benzopyran-2,4-piperidine; arylpiperazines including RWJ-38063, RWJ-68141, RWJ-68157, RWJ-69736, Ro-70-004, REC 15/2739, SB216469, urapidil and 5-methyl urapidil; dihydropyridines including SNAP 5089 and niguldipine; aminobenzodioxanes including WB 4101; dihydroindoles including RS17053 and KMD-3213, n-alkylated saccharins, and derivatives thereof.

In an embodiment, the ophthalmic formulation is orally administered.

In an embodiment, the ophthalmic formulation is administered in a topical manner.

In an embodiment, the ophthalmic formulation is administered from an eye dropper that contains the ophthalmic formulation.

In an embodiment, the ophthalmic formulation is administered from a contact lens on which the ophthalmic formulation is applied.

In an embodiment, the resultant pupil diameter ranges from about 6 mm or less.

In an embodiment, the resultant pupil diameter ranges from about 3 mm to about 5 mm.

In an embodiment, the resultant pupil diameter ranges from about 2.75 mm to about 4.0 mm.

In an embodiment, the pupil diameter at about 2 mm or less in a bright light is not effected.

In an embodiment, the pupil diameter is reduced by about 1 mm or more.

In an embodiment, a pupil area is reduced by about 20% or more.

In an embodiment, the compound further promotes corneal absorption over vascular effect via chemical modulation of a vascular tissue.

In another embodiment, the present invention provides a method of modulating pupil dilation. The method includes administering to an eye of an individual a formulation comprising a therapeutically effective amount of a compound that selectively effects an iris alpha adrenergic receptor over a vascular alpha adrenergic receptor; and allowing the formulation to remain in contact with the eye for a period of time in a reduced light where a dilator muscle of the eye receives greater stimulation in absence of the formulation.

In an embodiment, the formulation is administered in an amount so as to provide an optimized pupil diameter of about 6 mm or less.

In an embodiment, the optimized pupil diameter ranges from about 3 mm to about 5 mm.

In an embodiment, the optimized pupil diameter ranges from about 2.75 mm to about 4 mm.

In an embodiment, the optimized pupil diameter at about 2 mm or less in a bright light is not effected.

In an embodiment, a pupil diameter is reduced by about 1 mm or more to optimize pupil diameter.

In an embodiment, a pupil area is reduced by about 20% or more to optimize pupil diameter.

In an embodiment, the formulation is administered in an amount so as to reduce an adverse visual effect.

In an embodiment, the adverse visual effect is due to at least one of a perceived light scattering, a reduced contrast sensitivity and a reduced acuity.

In an embodiment, the adverse visual effect is due to an imperfect aspheric peripheral corneal curvature.

In an embodiment, the adverse visual effect is due to a higher order aberration of the eye, such as a coma, a secondary astigmatism, a spherical aberration, a trifoil, a quadrafoil, and a tetrafoil.

In an embodiment, the adverse visual effect is due to an uncorrected spherocylindrical correction contributed to by peripheral zones of a cornea.

In an embodiment, the compound includes an alpha 1a selective antagonist.

In an embodiment, the alpha 1a selective antagonist includes sulfonamides including tamsulosin; uracils including A-131701, fiduloxasin, Ro-70-004, urapidil and 5-methyl urapidil; piperidines including 4-oxospiro benzopyran-2,4-piperidine; arylpiperazines including RWJ-38063, RWJ-68141, RWJ-68157, RWJ-69736, Ro-70-004, REC 15/2739, SB216469, urapidil and 5-methyl urapidil; dihydropyridines including SNAP 5089 and niguldipine; aminobenzodioxanes including WB 4101; dihydroindoles including RS17053 and KMD-3213; n-alkylated saccharins; and derivatives thereof.

In yet another embodiment, the present invention provides a method of administering a formulation to an eye of an individual. The method includes administering a therapeutically effective amount of a compound within the formulation that selectively effects an iris alpha adrenergic receptor over a vascular alpha adrenergic receptor wherein the compound optimizes a pupil diameter while effectively minimizing eye redness.

In an embodiment, the formulation further promotes corneal absorption over vascular effect via a chemical modulation of a vascular tissue.

In an embodiment, the chemical modulation includes a temporary shielding or binding to a conjunctiva of the eye.

In an embodiment, the chemical modulation increases corneal absorption without effect on vascular absorption.

In an embodiment, the chemical modulation increases corneal absorption while decreasing vascular absorption.

In an embodiment, the chemical modulation occurs through exposure to one or more substances selected from the group consisting of a bioflavonoid, vitamin A, and substances derived from fruits and vegetables in order to reduce capillary permeability, including herbal extracts including aescin.

In an embodiment, the chemical modulation occurs through use of one or more substances selected from the group consisting of demulcents, herbal extracts, horse chestnut extracts, and a substance containing mucilage.

In an embodiment, a mucous membrane of the eye is protected from chemical irritants, to soothe the eye and/or to reduce redness, burning, stinging, or dryness by binding a protective layer to the mucous membrane of the eye and the conjunctiva.

In an embodiment, a mucous membrane of the eye is protected from chemical irritants, to soothe the eye and/or to reduce redness, burning, stinging, or dryness by reducing a capillary permeability of the eye and increasing a venous tone by using bioflavonoids.

In an embodiment, the chemical modulation occurs through a chemical modulator selected from the group consisting of an azone, a collagen corneal shield, a cyclodextrin including a charged cyclodextrin and a sulfated cyclodextrin, a bioadhesive polymer, a microsphere, a chitosan, a captisol and derivatives thereof.

In an embodiment, the chemical absorption is increased via one or more carrier particles selected from the group consisting of nanoparticles including liposomes and emulsions, dendrimers, and buckeyballs.

In an embodiment, the pupil diameter is optimized to about 6 mm or less.

In an embodiment, the pupil diameter is optimized to about 3.0 mm to about 5.0 mm in size.

In an embodiment, the pupil diameter is optimized to about 2.75 mm to about 4.0 mm.

In an embodiment, the pupil diameter at about 2 mm or less in a bright light is not effected.

In an embodiment, the pupil diameter is reduced by about 1 mm or more to optimize pupil diameter.

In an embodiment, the pupil diameter is optimized by reducing a pupil area by about 20%.

In an embodiment, the compound includes an alpha 1a selective antagonist that acts as a sole active ingredient to optimize pupil diameter.

An ophthalmic formulation of the present invention in an embodiment preferably obtains two simultaneous effects (a) reducing the amount of dilation the eye would normally undergo in a reduced light; and (b) reducing eye redness. Reducing normal dilation can be obtained by administering a compound which interferes with the normal stimulation of muscles which cause dilation. This can be done, for example, with an alpha 1 antagonist which may also cause redness, though if the alpha 1 antagonist is preferentially selective for the iris smooth muscle this will be lessened. However, redness may be reduced using an alpha 1 agonist. The antagonist and agonist will, in general, counteract each other. The present invention provides a particularly preferred formulation of (a) an alpha 1 antagonist which is an imidazoline, preferably phentolamine; and (b) an alpha 1 agonist which is either tetrahydrozoline and specifically tetrahydrozoline hcl; or other alpha agonists such as oxymetazoline, naphzoline or the like. While some of these compounds may slightly increase pupil size when used in the absence of an alpha antagonist this effect can be prevented in the presence of an alpha antagonist. Formulations of the invention provide preferred combinations of alpha-1-antagonists and alpha-1-agonists which reduce both dilation and redness. As previously discussed, a selective alpha 1 antagonist, such as tamsulosin or KMD 3213, can be used on its own to reduce pupil reflex while, at the same time, providing minimal, if any, eye redness according to another preferred embodiment of the present invention.

A formulation for optimizing pupil size in dim lighting conditions is disclosed according to an embodiment of the present invention. The formulation is preferably a solution of the type used in an artificial tear formulation having dissolved therein a therapeutically effective amount of a compound characterized by its ability to reduce dilation of the eye, particularly in dim light. The compound generally interferes with a natural biochemical reaction which results in the stimulation of the dilator muscles of the eye. In an embodiment, the formulation preferably includes a compound which reduces eye redness, e.g. tetrahydrazoline, oxymetazoline, naphzoline or the like. The compound which has the ability to disrupt endogenous compounds which stimulate dilator muscles of the eye may be an alpha 1 antagonist which belongs to a class of compounds which includes imidazolines such as phentolamine and tolamine. As previously discussed, the present invention also provides a single active component that can effectively reduce pupil light reflex to optimize vision while, at the same time, provide minimal, or effectively eliminate, redness to the eye upon application thereof, such as in a topical medication. In an embodiment, the single active component includes a selective alpha 1 antagonist, such as a selective alpha 1a antagonist.

A method of optimizing pupil diameter is disclosed wherein the pupil diameter in reduced light is effected so that it is not more than about 4 mm to about 5 mm, or about two to five times its diameter size in day light. The method encompasses administering a therapeutically effective amount of an alpha 1 antagonist, such as a selective alpha 1 antagonist, to an eye of a person in need thereof. The optimized pupil diameter in reduced light may be no more than about 5 mm, and the pupil diameter in bright light may be constricted no more than about 2 mm or even as small as about 1 mm. Further, the optimized pupil diameter in reduced light may be between and including about 3 mm and about 5 mm, preferably about 3 mm to about 4 mm and may vary with different patients. Actual results with human patient's are shown in the Examples as described below. A reduction of pupillary size of 1 mm or greater compared to whatever an individual's normal pupil size is in reduced light, however, is sufficient to establish a clinically useful effect pursuant to an embodiment.

The results show that alpha-1-antagonists can reduce dilation but that some alpha-1-antagonists also cause significant redness of the eye. In an embodiment, the reduction in dilation is about 1.0 mm or greater. The formulations and methodologies of the present invention provide reduced pupil diameter with effectively no redness or acceptable levels of redness. This can be achieved with the use of an alpha 1 selective antagonist acting as a sole active ingredient pursuant to an embodiment of the present invention. In an embodiment, the amount of pupil area can be effectively reduced by about 20% or greater thereby enhancing vision.

In accordance with the method of the present invention, in an embodiment, an application device such an eyedropper is utilized in order to apply a therapeutically effective amount of an alpha 1 antagonist to the eye of a patient which is preferably the eye of a human patient and more preferably a substantially unmedicated human eye. Thereafter, the formulation is allowed to effect the pupil of the eye and contract the pupil so that the pupil does not expand above a level which is two to five times the diameter of dilation when the eye of the patient is present in bright light in an embodiment. Accordingly, another aspect of the present invention is a formulation comprised of an aqueous solution having an alpha 1 antagonist such as an imidazoline, an alpha 1 selective antagonist, and the like, present therein wherein the formulation is present in an eyedropper. As used herein, the "term eyedropper" includes any suitable type of eyedropper including, for example, plastic form/fill/seal containers that are squeezed to produce drops.

The present invention, in an embodiment, is also directed to a method for optimizing pupil diameter in a reduced light by minimizing its dilatation in response to less light, comprising administering a therapeutically effective amount of an alpha 1 antagonist, such as an alpha 1 selective antagonist, to an eye of a person in need thereof. In this method, dilatation of the pupil diameter in a reduced light may be minimized in response to less light compared with bright light, and the method may not induce ciliary muscle contraction.

In the method of the present invention in an embodiment, the patient may suffer from excessively large pupils in a reduced light, and the patient may suffer from poor quality of vision, and the patient may be undergoing medication that results in dilation of the pupil diameter. Alternatively, the pupil diameter of the patient may be naturally excessively dilated as a result of an excessive genetically programmed response to dimming of light. In addition, the patient may use nutritional supplements or stimulants, or require use of oral medications, that as a side effect increase the pupil diameter in a reduced light, such as caffeine, antihistamines and products containing stimulants such as ephedra or other epinephrine like compounds.

The present invention in an embodiment includes a treatment method wherein the eye drop formulation of the present invention is administered to the eye(s) of a human patient each night before going to sleep. The formulation remains effective for about 20 hours and as such is required to be administered once a day, such as when administered each morning, according to an embodiment of the present invention.

The method of the present invention in an embodiment may be carried out by directly instilling onto the eye an eye drop formulation of the present invention according to an embodiment. Optionally, the alpha 1 antagonist may be administered by contacting a contact lens, and the contact lens applied to the eye pursuant to an embodiment. As a soft contact lens has a varied water content often ranging from about 40% to 70%, an aqueous soluble compound is easily applied when in this reservoir, with the advantage of prolonged exposure to corneal absorption. In the method of the present invention, the used alpha 1 antagonist preferably may belong to a class of compounds referred to as imidazolines and particularly to phentolamine according to an embodiment. As previously discussed, an alpha 1 selective antagonist, such as tamsulosin, or KMD-3213, can be used as a single active component of the ophthalmic formulation according to an embodiment.

The present invention in an embodiment is directed to a method for reducing pupil diameter in a reduced light in cases where dilation of the pupil is excessive, such as about 6 mm or greater. However, reducing dilation even from about 8 mm to less than about 7 mm can improve visual function for an individual with about 8 mm pupils in a reduced light. As a result, the pupil area can be effectively reduced to enhance vision. In an embodiment, the pupil area is reduced about 20% or greater. Administering a formulation of the present invention does not induce ciliary contraction or undesirable pseudomyopia that may result from taking certain medications like pilocarpine. Formulations disclosed herein reverse mydriasis (i.e., dilation) which results after the administration of parasympatholytic agents. Formulations of the invention are also effective on agents paralyzing accommodation such as 1% cyclogyl, which can then be used for more complete cycloplegia and accurate prelaser refractive measurement.

The present invention recognizes that alpha 1 antagonists which are typically used for treatment of high blood pressure, treatment of pheochromocytoma, migraines, bladder spasm, prostate enlargement, sexual dysfunction and the like can be formulated and used in reducing pupil diameter in a reduced light, thereby enhancing pupil light reflex.

The present invention provides an ophthalmic composition which achieves the combined requirements of reduced redness and pupil diameter optimization.

Alpha adrenergic receptor antagonists function to block alpha 1 receptor mediated contraction of arterial and venous smooth muscle. Alpha-2 adrenergic receptors are involved in suppressing sympathetic output, increasing vagal tone, facilitating platelet aggregation, inhibiting the release of norepinephrine and regulating metabolic effects. Alpha adrenergic antagonists have a wide spectrum of pharmacological specificities and are chemically heterogeneous. See, for example, Goodman & Gillman's "The Pharmacological Basis of Therapeutics" (Ninth Edition) at pages 225-232 in particular.

The chemical classes of alpha-1-antagonists include, for example, alkylating agents, imidazolines, piperazinyl quinazolines, indoles and the like. Many have both alpha 1 and alpha-2 receptor antagonist activity. The indoles provide alpha-2 activity and are not believed to be clinically useful in reducing pupil dilation.

Alkylating agents provide effectiveness for reversing pharmacologic mydriasis, but are only modestly effective for minimizing pupillary dilation. However, these compounds produce unacceptably high levels of eye redness with severe blood vessel dilation causing fluid leakage and swelling of the conjunctiva known as chemosis. The best use is in veterinary medicine to reverse cyclopegia in animal eyes.

The piperazinyl quinazolines, such as prazosin and dapiprazole, have a modest effect on pupil diameter in dim light. However, they are believed to be less clinically effective as compared to imidazolines, with prazosin more effective than dapiprazole, which is believed to have minimal if any clinically significant effect. Dapiprazole also causes unacceptably high levels of eye redness with severe blood vessel dilation, thereby causing fluid leakage and swelling of the conjunctiva (chemosis). A longer lasting, more potent piperazinyl quinazoline may be clinically effective, but its side effects shortcomings would have to be overcome.

Phentolamine is not as strong an alpha 1 receptor antagonist as prazosin. However, imidazolines such as phentolamine have other related properties beyond alpha 1 antagonism. Further, any alpha antagonist which by its structure preferentially effects iris smooth muscle more or vascular tissue less will have improved clinical efficacy to the extent the iris and vascular alpha 1 adrenergic receptors vary in an individual. This difference may account for the varying relationship between conventional understanding of potency, which is often related to the cardiovascular effects, and the ophthalmic derivation of the present invention.

Other properties include blocking receptors for 5-HT, release of histamine from mast cells, and blockage of K+ channels. Imidazolines provide long lasting reduction in pupil dilation without causing unacceptably high levels of redness. Used at night before sleep they produce about 20 hours of effect; used on arising they are generally effective for about 24 hours as the patient is generally sleeping during the last few hours, i.e., sleeping during hours 20-24 after administration pursuant to an embodiment of the present invention.

As previously discussed, the present invention provides an ophthalmic formulation that includes a single active component that is selective for iris alpha receptors as compared to vascular alpha receptors. This provides effective reduction in pupil size in a reduced light while, at the same time, causing minimal, if any, redness in response to application thereof to the eye, such as in a topical manner. In an embodiment, the single active component includes a selective alpha 1 antagonist.

The compounds that are selective for iris alpha receptors as compared to vascular alpha receptors can include a variety of different and suitable compounds. For example, classes of compounds and specific types of compounds can include sulfonamides including tamsulosin; uracils including A-131701, fiduloxasin, Ro-70-004, urapidil and 5-methyl urapidil; piperidines including 4-oxospiro benzopyran-2,4-piperidine; arylpiperazines including RWJ-38063, RWJ-68141, RWJ-68157, RWJ-69736, Ro-70-004, REC 15/2739, SB216469, urapidil and 5-methyl urapidil; dihydropyridines including SNAP 5089 and niguldipine; aminobenzodioxanes including WB 4101; dihydroindoles including RS17053 and KMD-3213, n-alkylated saccharins, derivatives thereof, and the like.

An aspect of the present invention is an ophthalmic formulation comprised of an aqueous solvent and an alpha 1 antagonist, such as an imidazoline or an alpha 1 selective antagonist, in an embodiment. The aqueous solvent may, in its simplest form, be water but is preferably a solvent that includes an ophthalmic artificial tear solution. The alpha 1 antagonist in an embodiment is preferably present in a relatively low concentration, such as less than about 1% concentration. For example, the alpha 1 antagonist may be present in an amount in the range of about 0.01 milligram per cubic centimeter of aqueous solvent to about 50 milligram per cubic centimeter of solvent. Another aspect of the present invention in an embodiment is the formulation contained within an application device such as a conventional or improved eyedropper of the type described herein. Alternatively, a mucin or mucinous agent may be used to bind preferentially to the conjunctival surface and minimize vascular absorption while corneal absorption of the active ingredient is thereby occurring with little adverse effect. Similarly, a demulcent may be used for this protective purpose. -Demulcent herbs have the effect of acting as a protective barrier on irritated or inflamed tissue. When they are used on the skin, demulcents are called emollients. The experience of demulcency cannot always be explained pharmacologically. They contain complex polysaccharide molecules of mucilage that have the property of becoming slimy and gummy when in contact with water. This may offer protection to the conjunctiva of the eye when applied topically, and minimize absorption of the active ingredient alpha 1 antagonist by the conjunctiva.

An aspect of the present invention in an embodiment is an ophthalmic formulation that includes an imidazoline in an artificial tear carrier.

Another aspect of the present invention in an embodiment is a method of treatment whereby an imidazoline is applied to a human eye in an amount sufficient to reduce pupil dilation.

Yet another aspect of the present invention in an embodiment is a formulation that includes an alpha-1-antagonist (e.g., phentolamine) and an alpha-1-agonist (e.g., tetrahydrazoline).

An advantage of the present invention is to treat patients who have been subjected to laser surgery and have developed a range of different vision problems as a result of excessive dilation of their pupils relative to the effective size of their laser surgery created optical zone.

Another advantage of the present invention is that the ophthalmic formulations can be formulated in a manner which is readily administered to the eye to obtain a desired effect.

Yet another advantage of the present invention is to provide an ophthalmic formulation with a single active component that can effectively optimize pupil light reflex to improve vision while, at the same time, provide minimal, if any, redness to the eye upon application thereof.

Additional features and advantages of the present invention are described in, and will be apparent from, the following Detailed Description of the Invention and the figures.

DETAILED DESCRIPTION OF THE INVENTION

Figure 1:
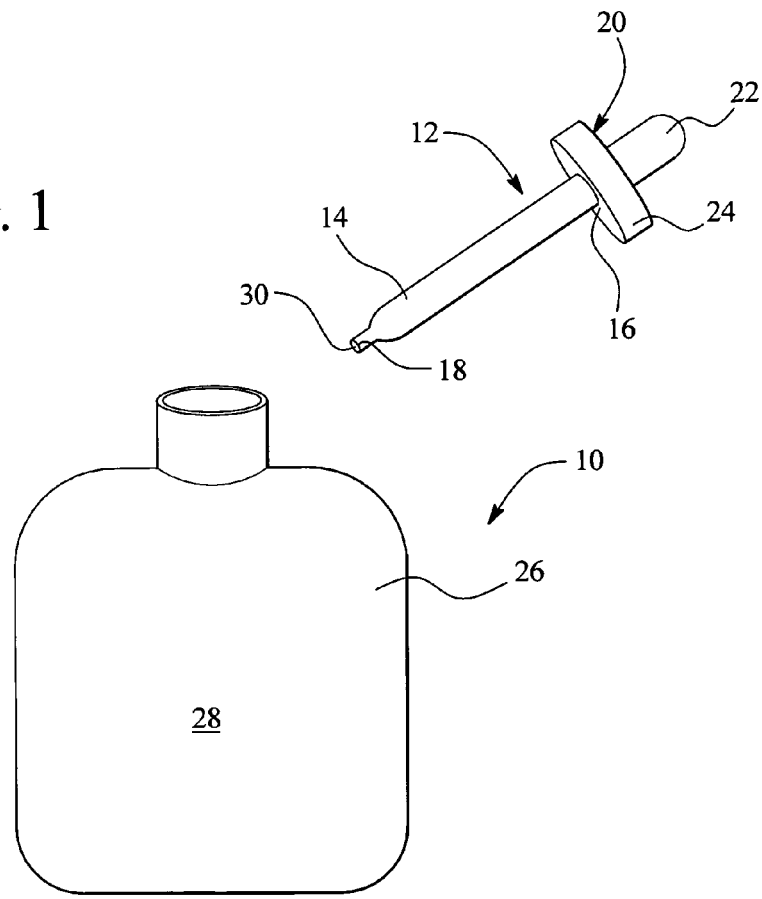
FIG. 1 schematically illustrates an eyedropper apparatus according to an embodiment of the present invention.

The present invention relates to ophthalmic formulations. In general, the ophthalmic formulations can effectively act to reduce excessive pupil dilation, particularly in a reduced light including absent lighting.

In an embodiment, the ophthalmic formulations of the present invention antagonistically effect the alpha 1 adrenergic receptors of the iris over the conjunctival vessels. When light illumination is reduced, reduced pupil dilation results compared to the genetic predisposition of the treated subject. A pupil dilation in a reduced light from about 3 mm to about 5 mm is preferred, as compared to a pupil dilation from about 1 mm to about 2 mm in a bright light. This can provide from about two to about sixteen times more pupil surface area in a reduced light as compared to pupil surface area in a bright light. Since the mean pupil in a reduced light is about 6 mm within a range from about 3 mm to about 9 mm, many individuals can obtain a more ideal pupil size under a reduced light, such as mesopic or scotopic conditions, that is closer to about 3 mm to about 4 mm using a selective alpha antagonist in an ophthalmic formulation according to an embodiment of the present invention.

The degree of optical imperfections in a subject's eye will determine the magnitude of improved quality of night vision. However, such imperfections are exceedingly common. For example, a range of about 25% to about 40% of subjects questioned about their quality of night vision prior to undergoing laser vision correction in FDA monitored and controlled studies indicate poor night vision and/or glare, halo, and difficulty driving at night before undergoing laser vision correction.

In an embodiment, the ophthalmic compositions include an alpha 1 antagonist. Preferably, the compositions include a sub-class of alpha 1 antagonists that include selective alpha 1 antagonists also referred to herein as alpha 1 selective antagonists or the like. This class of compounds can preferentially effect iris alpha adrenergic receptors over vascular alpha adrenergic receptors in a reduced light as previously discussed. In this regard, the selective alpha 1 antagonists can effectively act to reduce the pupil light reflex in a reduced light of an eye while minimizing dilation of conjunctival and/or scleral vessels, thus effectively eliminating an undesirable redness response to a therapeutic amount of the selective alpha 1 antagonist applied to the eye, such as in a topical manner.

Characteristics of the Eye

It is well known that pupillary dilation in a reduced light is a teleologic adaption to allow more light to enter our eyes. Along with adaptions on the retina to scotopic, or night vision, this allows increased useful acuity over a very large range of dim light situations. It is also well known that only very small pupillary openings are consistent with a large field of vision, as occurs for example in bright sunlight with about 1 mm pupillary openings. Less well known is the dramatic range that exists among human beings of the degree to which pupils will dilate in a reduced light, ranging from maximal dilation in complete darkness of as little as about 3 mm in some individuals to as high as about 9 mm in others. This difference is part of the genetic makeup of an individual. In this regard, a pupil at about 3 mm in size provides sufficient added light in a reduced light relative to a pupil size of about 1 mm to about 2 mm in daylight. What is less well known is that unless a pupil in darkness is less than about 3 mm, there is no perceived increase in darkness. It is therefore this range in pupil size of about 3 to about 4 mm that is the ideal pupil size in darkness according to an embodiment of the present invention. Larger pupils in a reduced light can allow more extraneous light increasing light scatter. This reduces contrast, reduces acuity, and causes glare and halo effect in some cases, with little or no clinical benefit.

When living in literal total darkness, there may have been a very slight advantage for our evolutionary ancestors to have larger pupil diameters in a reduced light. However, but whatever advantage was conferred has been lost once several advances in civilization resulted in illumination; including, for example, artificial means of background lighting, neon lights to allow signs to be more easily read, fluorescent light with its weighted blue more highly scattering component, point sources of light caused by car headlights, traffic lights and the like. These light sources are visible at optimal quality when sufficient corneal diameter exists to allow light to enter, such as a pupil size at about 3 mm, but not an excessive pupil size, as less corneal diameter is used to refract light, as less light scatter is induced than pupils at about 5 mm to about 6 mm or larger in size. Optimized pupil size in a reduced light according to an embodiment of the present invention ranges from about 2 millimeters (mm) to about 6 mm, preferably about 3 mm to about 5 mm, and more preferably about 3 mm to about 4 mm.

In an embodiment, the formulations of the present invention can selectively reduce pupil size by about 1 mm or greater. This effectively equates to a reduction in pupil area of about 20% or greater. As previously discussed, the present invention contemplates the use of a single active agent, preferably an alpha 1a selective antagonist that can optimize pupil light reflex while minimizing, if not eliminating, redness.

The peripheral corneal curvature in many people is not in perfect curvature alignment with that of the central cornea. In individuals with small to moderate pupils in a reduced light, the pupil acts as a filter so that the peripheral cornea in these cases is not a factor. But, for larger pupils in a reduced light, peripheral corneas may be either too steep or too flat in many cases relative to the central curvature, causing spherical aberration. These corneas are technically referred to as either prolate or oblate when imperfect. The eye drops of the present invention in an embodiment clinically eliminate the adverse effects of virtually all such spherical aberration, as the peripheral corneal curvature outside of a central optical zone at about 4 mm to about 5 mm in size are filtered by the treated smaller pupil in reduced light and the extraneous light focused by the spherical aberration is eliminated.

Pupils at about 3 mm in size are sufficiently large to allow sufficient light to enter the eye in scotopic situations or other reduced light environments, yet provide excellent filters to minimize light scatter of ambient artificial light and/or point sources of light. Pupils at about 9 mm in size, on the other hand, utilizing nine times more corneal surface area than a 3 mm pupil, can induce considerable light scatter of point sources, neon lights, and fluorescent blue light. While the current state of the art within the ophthalmic and optometric professions does not generally recognize this distinction, and wherein refractive surgery standard of care does not generally recognize a distinction in pupil diameter in dim light as a predictive factor in outcome, use of the novel pharmacologic method of the present invention has demonstrated this to be so in clinical use.

As shown below, Tables 1 and 2 demonstrate the results of a study of several different alpha adrenergic antagonists on several patients, with different parameters being measured. The results show that several alpha adrenergic antagonists reduced dilation when applied to a human eye. However, only the imidazolines obtain the desired reduction in dilation without causing excessive redness of the eye. In addition, the present invention in an embodiment provides a sub-class of alpha antagonists that can act as a sole active component in an ophthalmic medication to effectively reduce pupil light reflex while providing minimal, if any, redness response upon application thereof to the eye. In an embodiment, the sub-class of alpha antagonists includes alpha 1 selective antagonists, including alpha 1a selective antagonists, such as tamsulosin.

Refractive optical aids, such as glasses or contact lenses, increase the degree of light scatter in scotopic situations by adding optical elements that are imperfect in that they have surfaces that scatter light. Refractive surgery on the cornea, whereby a change in contour is induced by surgical means that can include incision (RK), laser ablation (Lasik, PRK), or prosthesis (e.g., plastic segments inserted into the cornea) also adds imperfections that increase the degree of light scatter in scotopic conditions. The variables of pupil size in reduced light and refractive optics adding to light scatter has created circumstances in which individuals have quality of vision difficulty navigating in scotopic situations as a result of glare, halo, and related distortions at night or in dimly lit environments of any kind.

The present invention in an embodiment is particularly useful in treating patients who have been subjected to various types of refractive surgery as described above. Because such surgery can increase the degree of light scatter, the administration of the formulation of the present invention can modulate this effect by contracting the pupil. Thus, the present invention includes carrying out refractive surgery on a patient and thereafter administering a formulation according to an embodiment to the patient over time as needed, such as to maintain the pupil size at about 2 mm to about 5 mm, preferably about 3 mm to about 5 mm and more preferably about 3 mm to about 4 mm. The formulation of the present invention in an embodiment may be administered periodically on a daily basis, such as once daily, twice daily, or as needed, and particularly, administered in situations where the patient is subjected to a reduced light.

The term "reduced light" or other like terms as used herein, such as "dim light" and the like, refers to a light environment wherein the pupils of the patient are dilated to a substantially maximum amount. This includes an environment absent of light. Alternatively, the term "bright light" or other like term is used herein to describe a surrounding light environment wherein the pupil of the patient's eye is contracted maximally, such as dilated to a minimum amount. The term "bright light" suggests lighting derived from, for example, indoor lighting, the outdoor lighting, mid-day lighting, no cloud lighting, and the like. An aspect of the present invention is that the formulation in an embodiment can limit pupil dilation to about two to about twenty-five times pupil area in reduced light as compared to the pupil area which would occur in bright light.

In an embodiment, the method of the present invention utilizes a novel pharmacologic mechanism of optimizing pupil size by reducing pupil size in dim light. Conventional teaching of eye specialists has been to use constricting agents of the pupil, such as acetylcholine or cholinesterase inhibitors to reduce pupil size. Using dilute concentrations of such agents, it is possible to constrict the pupil and create improved viewing for affected individuals in scotopic environments. However, undesirable side effects of such medications, including excessive constriction initially causing severe dimming, brow ache, generalized pain, redness, and induced blurring secondary to ciliary accommodation, severely limits the value of these classes of pharmacologic agents. Retinal detachment is a known rare complication of its use.

Pharmaceutically Active Component

The pharmacologic method of the present invention in an embodiment utilizes a class of compounds known as alpha 1 antagonists to inhibit pupillary dilation in reduced light, such as under scotopic conditions preferentially over constriction of the pupil, thus affecting the dilator muscles of the iris preferentially, and has effectively no clinically significant effect on the ciliary muscle responsible for accommodation. This class of compounds has been used to treat hypertension, prevent bladder spasmodic contractions and improve urinary outflow, and treat prostate enlargement.

A significant feature of the present invention in an embodiment is to employ a particular class of alpha antagonists, particularly imidazolines to allow improvement in vision quality in a reduced light effectively without causing either excessive redness or negative clinical effects in normal lighting conditions. Additionally, another feature of the present invention is to reverse the effects of parasympatholytics more effectively than dapiprazole.

In addition to imidazolines, the present invention in an embodiment provides an ophthalmic formulation that includes a sole active ingredient derived from a sub-class of alpha 1 antagonists, preferably, alpha 1 selective antagonists, such as alpha 1a selective antagonists. This sub-class of alpha 1 antagonists can preferentially act on the iris alpha adrenergic receptors over vascular alpha adrenergic receptors. This provides effective reduction in pupil light reflex for improved vision while, at the same time, providing minimal, if any, redness response upon application thereof. The present invention contemplates the use of any suitable type and amount of alpha 1 selective antagonist, such as sulfonamides including tamsulosin; uracils including A-131701 (ABBOTT), fiduloxasin (ABBOTT), Ro-70-004, urapidil and 5-methyl urapidil; piperidines including 4-oxospiro benzopyran-2,4-piperidine; arylpiperazines including RWJ-38063 (R.W. Johnson Research Institute), RWJ-68141 (R.W. Johnson Research Institute), RWJ-68157 (R.W. Johnson Research Institute), RWJ-69736 (R.W. Johnson Research Institute), Ro-70-004, REC 15/2739, SB216469, urapidil and 5-methyl urapidil; dihydropyridines including SNAP 5089 and nigulpidine; aminobenzodioxanes including WB 4101; dihydroindoles including RS17053 and KMD-3213 (KISSEI PHARMACEUTICAL); and n-alkylated saccharins; and derivatives thereof. RS17053 is generally known and not limited to having a chemical name of (N-[2-(2-cyclopropylmethoxyphenoxy)ethyl]-5-chloro-α,α-dimethyl-1H-indole-3-ethanamine) or other suitably known chemical name, such as N-[2-(2-cyclopropylmethoxyphenoxy)ethyl]-5-chloro-alpha,alpha-dimethyl-1H-indole-3-ethanamine hydrochloride and KMD-3213 is the active ingredient in commercailly-available RAPAFLO® (silodosin) and generally known and not limited to having a chemical name of 1-(3-Hydroxypropyl)-5-[(2R)-2-({2-[2-(2,2,2-trifluoroethoxy)phenoxy]ethy}amino)propyl]-2,3-dihydro-1H-indole-7-carboxamide or other suitably known chemical name, such as (−)-(R)-1-(3-hydroxypropyl)-5[2-[2-(2,2,2-trifluoroethoxy)phenoxy]ethyl]amino]propyl]indoline-7-carboxamide and 1-(3-hydroxypropyl)-5-(2-(2-(2-(2,2,2-trifluoroethoxy)phenoxy)ethylamino)propyl)indoline-7-carboxamide.

A formulation of the present invention in an embodiment can be used to optimize pupil size to obtain enhanced vision acuity in reduced light by reducing the pupil diameter effectively, without causing a clinically significant reduction in pupil size in bright light, particularly when the pupil size does not need to be reduced to some extent as required under reduced light.

Formulations of the present invention in an embodiment include two active compounds. The first active compound is an antagonist which blocks the effect of an endogenous compound which stimulates a dilator muscle of a human eye. In an embodiment, the antagonist is an alpha 1 antagonist, such as a nonselective alpha 1 antagonist including phenoxybenzamine and phentolamine. The second active compound is an agonist which (a) does not substantially interfere with antagonists and thus allows for iris dilation to be blocked and (b) prevents or reduces redness. The first active compound is preferably an imidazoline, more preferably phentolamine. The second active compound is preferably tetrahydrazolene, more preferably tetrahydrazolene hcl, oxymetazoline, naphzoline or other redness reducer.

In another embodiment, the formulation of the present application includes a single active component that can act to reduce pupil size in a reduced light while minimizing, or effectively eliminating, an undesirable redness response to application thereof, such as in a topical manner. Preferably, the single active component includes an alpha selective antagonist, such as an alpha 1 selective antagonist including alpha 1a selective antagonists, such as tamsulosin or the like as previously discussed.

According to the present invention in an embodiment, the optimized pupil diameter in reduced light is no more than about two to five times greater than that in bright light.

Thus, it will be understood by those skilled in the art reading this disclosure that the formulation of the present invention in an embodiment decreases the difference between the diameter of pupil dilation in reduced light and the diameter of pupil dilation in bright light. This is done by decreasing the amount of dilation the human eye will undergo when exposed to reduced light.

While the ophthalmic composition of the present invention in an embodiment can be used to optimize pupil size under any circumstances, the composition of the present invention is administered to the eye of an individual to reduce naturally occurring pupillary dilation in reduced light, especially in situations where the dilation is sufficiently excessive so as to have a measurable effect on vision acuity. The composition of the invention can be used also to counteract pupil dilatation caused by medication according to an embodiment.

As used herein, the term "active agent" or other like terms including, for example, active component, is a pharmaceutically acceptable compound which when applied to the eye acts on an iris smooth muscle dilator. More preferably, the active agent is of a particular class of alpha 1 antagonists, such as imidazolines, including phentolamine, alpha 1 selective antagonists including tamsulosin and the like.

Imidazolines are compounds having the following general structural formula:

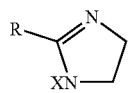

wherein x is any positively charged moiety and is preferably H, Ca, Na, Mg or an amine in preferably H, and R is an alkyl or substituted alkyl containing 1 to 18 carbons wherein the substitutions are preferably OH and N, and wherein R is preferably

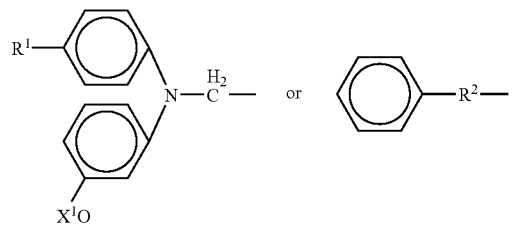

wherein $R^1$ is a lower alkyl containing 1 to 6 carbons and may be a straight chain, branched or cyclical alkyl and is preferably —CH3 and $X^1$, is a positively charged moiety and preferably —H and $R^2$ is an alkyl containing 1 to 6 carbons and is preferably —CH$_2$—.

Alpha 1 antagonists are currently used to treat pheochromocytoma, a condition in which alpha receptor stimulants, such as epinephrine and norepinephrine, are released throughout the body in extremely high concentration.

Examples of alpha 1 antagonist are disclosed within issued U.S. Pat. No. 6,046,207 issued Apr. 4, 2000. Other examples are disclosed within U.S. Pat. Nos. 5,891,882 and 5,792,767. The above cited three U.S. patents are incorporated herein by reference to disclose alpha 1 antagonist. Further, publications cited in these patents are incorporated herein by reference in order to disclose and describe therapeutically effective compounds which can be formulated and used in connection with the present invention when used in appropriate ophthalmic formulations and applied directly to the eye of a patient to effect pupil dilation.

Those skilled in the art reading this disclosure will recognize that an active compound can be any pharmaceutically acceptable compound which disrupts (i.e., blocks the biochemical interactions or reactions) endogenous compounds which stimulate dilator muscles of a human eye. Compounds other than alpha-1-antagonists can be tested as described here and it will be noted (as shown in the results of Table 1) that not all alpha 1-antagonists provide pharmaceutically acceptable results (when applied alone) even when endogenous compounds which stimulate dilator muscles of a human eye are blocked and dilation is reduced. For example, phenoxybenzamine (an alpha-1-antagonist) will reduce dilation but causes an unacceptably high level of redness in the treated eye when applied as the only active compound. As previously discussed, the present invention in an embodiment includes a sub-class of alpha 1 antagonist, such as alpha 1 selective antagonists that can preferentially act on the iris alpha adrenergic receptors over the vascular alpha adrenergic receptors and thus can be effectively utilized as a sole active agent to improve vision according to an embodiment of the present invention.

According to the present invention in an embodiment, an ophthalmic composition containing an active agent, such as an imidazoline, an alpha 1 selective antagonist and the like, is advantageously applied topically to the eye, especially in the form of a solution, a suspension, an ointment, a gel or coated on or absorbed into a solid insert or contact lens. Such compositions include the active ingredient, for example, in a range of from approximately about 0.01 milligrams per cubic centimeters (cc) of total formulation to approximately 50 milligrams per cc, preferably from approximately 0.05 milligrams per cc to approximately 20 milligrams per cc, or more preferably in the range of from approximately 0.1 milligrams per cc to approximately 10 milligrams per cc and most preferably in the range of from 1 milligram per cc to 5 milligrams per cc of total formulation volume. The dose of the active ingredient may depend on various factors, such as mode of administration, age and/or the condition of the eye being treated.

A preferred concentration of about 1 to about 5 milligrams of active agent per cc of total formulation volume in an embodiment may be administered by placing a single drop on a moist soft contact lens, and inserting the lens for about 15 minutes to about 45 minutes at one time per day. Administered in this manner an active agent such as imidazoline including phentolamine has a 20-24 hour clinical effectiveness. Phentolamine appears to have cumulative affect, such that with regular usage administration every other day (e.g., 48 hours) via the contact lens may be all that is necessary for some patients. The contact lens dosing allows for preferential absorption within the cornea, maximizing drop utilization and minimizing mild redness that may otherwise occur as well as the remote risk of systemic absorption. The amount of active agent in an embodiment within 1 drop of topical formulation, such as less than 0.10 mg, is about 50× less than the clinically recommended dosing for systemic results on the cardiovascular system. If 10% of the active agent reached systemic circulation, it would result in 500× less than typical clinical dosage. Using contact lens dosing, this is estimated to be still less. The drop may be administered in a one to five milligram per cc concentration directly to the eye as a recommended daily or BID dosing according to an embodiment of the present invention.

It should be appreciated that any suitable type of contact lens can be utilized for formulation administration purposes. In general, the formulation including the active agent is absorbed by the contact lens. This can allow a slow release of the active agent over the corneal surface over time. In an embodiment, the contact lens has a water content greater than about 10%, preferably ranging from about 20% to about 80%, more preferably ranging from about 30% to about 70%.

An effective active agent for the purpose of the present invention should limit pupil dilation and not significantly effect pupillary constriction. Further, the active agent should have significantly more effect and cause significantly increased percentage reduction in pupil diameter in patients with large pupils in reduced light, (e.g., in patients whose reduced light pupil exceeds their daylight pupil considerably) and much less effect on pupil diameter in patients who have a more idealized pupil diameter in reduced light (e.g., in patients where their reduced light pupil is nearly equal to their daylight pupil) as shown below, for example, in Table 2.

There are used for a corresponding ophthalmic composition customary pharmaceutically acceptable excipients and additives known to the person skilled in the art, for example those of the type mentioned below, especially carriers, stabilizers, solubilizers, tonicity enhancing agents, buffer substances, preservatives, thickeners, complexing agents and other excipients. Examples of such additives and excipients can be found in U.S. Pat. Nos. 5,891,913, 5,134,124 and 4,906,613.

Formulations of the present invention in an embodiment are prepared, for example by mixing the active agent with the corresponding excipients and/or additives to form corresponding ophthalmic compositions. The active agent is preferably administered in the form of eye drops, the active agent being conventionally dissolved, for example, in a carrier. The solution is, where appropriate, adjusted and/or buffered to the desired pH and, where appropriate, a stabilizer, a solubilizer or a tonicity enhancing agent is added. Where appropriate, preservatives and/or other excipients are added to an ophthalmic formulation of the invention.

Carriers used in accordance to an embodiment of the present invention are typically suitable for topical or general administration, and are for example water, mixtures of water and water-miscible solvents, such as C1- to C7-alkanols, vegetable oils or mineral oils including from about 0.5% to about 5% by weight hydroxyethylcellulose, ethyl oleate, carboxymethylcellulose, polyvinylpyrrolidone and other nontoxic water-soluble polymers for ophthalmic uses, such as, for example, cellulose derivatives, such as methylcellulose, alkali metal salts of carboxymethylcellulose, hydroxymethylcellulose, hydroxyethylcellulose, methylhydroxypropylcellulose and hydroxypropylcellulose, acrylates or methacrylates, such as salts of polyacrylic acid or ethyl acrylate, polyacrylamides, natural products, such as gelatin, alginates, pectins, tragacanth, karaya gum, xanthan gum, carrageenin, agar and acacia, starch-derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. Preferred carriers include, for example, water, cellulose derivatives, such as methylcellulose, alkali metal salts of carboxymethylcellulose, hydroxymethylcellulose, hydroxyethylcellulose, methylhydroxypropylcellulose and hydroxypropylcellulose, neutral Carbopol, or mixtures thereof. The concentration of the carrier ranges, for example, from about 1 to about 100,000 times the concentration of the active ingredient.

The solubilizers used for an ophthalmic composition of the present invention in an embodiment include, for example, tyloxapol, fatty acid glycerol poly-lower alkylene glycol esters, fatty acid poly-lower alkylene glycol esters, polyethylene glycols, glycerol ethers vitamin E and vitamin E derivatives, such as Vitamin E Tocopherol Polyethylene Glycol 1000 Succinate (TPGS) or mixtures of those compounds. A specific example of an especially preferred solubilizer is a reaction product of castor oil and ethylene oxide. Reaction products of castor oil and ethylene oxide have proved to be particularly good solubilizers that are tolerated extremely well by the eye. Another preferred solubilizer is tyloxapol. The concentration used depends especially on the concentration of the active ingredient. The amount added is typically sufficient to solubilize the active ingredient. For example, the concentration of the solubilizer ranges from about 0.1 to about 5000 times the concentration of the active ingredient pursuant to an embodiment of the present invention.

According to an embodiment of the present invention lower alkylene means linear or branched alkylene with up to and including seven carbon atoms. Examples are methylene, ethylene, 1,3-propylene, 1,2-propylene, 1,5-pentylene, 2,5 hexylene, 1,7-heptylene and the like. Lower alkylene is preferably, such as linear or branched alkylene, with up to and including four carbon atoms.

Examples of buffer substances are acetate, ascorbate, borate, hydrogen carbonate/carbonate, citrate, gluconate, lactate, phosphate, propionate, perborate TRIS (tromethamine) buffers and the like. Tromethamine and borate buffer are preferred buffers. The amount of buffer substance added is, for example, that necessary to ensure and maintain a physiologically tolerable pH range. The pH range is typically in the range of from about 5 to about 9, preferably from about 6 to about 8.2 and more preferably from about 6.8 to about 8.1.

Tonicity enhancing agents are, for example, ionic compounds, such as alkali metal or alkaline earth metal halides, such as, for example, $CaCl_2$, KBr, KCi, LiCI, NaI, NaBr or NaCl, or boric acid and the like. Non-ionic tonicity enhancing agents are, for example, urea, glycerol, sorbitol, mannitol, propylene glycol, dextrose and the like. For example, sufficient tonicity enhancing agent is added to impart to the ready-for-use ophthalmic composition an osmolality of approximately from about 50 mOsmol to about 1000 mOsmol, preferred from about 100 mOsmol to about 400 mOsmol, more preferred from about 200 mOsmol to about 400 mOsmol and even more preferred from about 280 mOsmol to about 350 mOsmol. Examples of preservatives are quaternary ammonium salts, such as cetrimide, benzalkonium chloride or benzoxonium chloride, alkyl-mercury salts of thiosalicylic acid, such as, for example, thimerosal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, or sorbic acid and the like. Preferred preservatives are cetrimide, benzalkonium chloride, benzoxonium chloride, parabens and the like. Where appropriate, a sufficient amount of preservative is added to the ophthalmic composition to ensure protection against secondary contaminations during use caused by bacteria and fungi.

Ophthalmic formulations of the present invention can also include, for example, non-toxic excipients, such as, for example, emulsifiers, wetting agents or fillers, such as, for example, the polyethylene glycols designated 200, 300, 400 and 600, or Carbowax designated 1000, 1500, 4000, 6000 and 10,000 and the like. Other excipients that may be used if desired are listed below but they are not intended to limit in any way the scope of the possible excipients. They are especially complexing agents, such as disodium-EDTA or EDTA, antioxidants, such as ascorbic acid, acetylcysteine, cysteine, sodium hydrogen sulfite, butyl-hydroxyanisole, butyl-hydroxytoluene or alphatocopherol acetate; stabilizers, such as a cyclodextrin, thiourea, thiosorbitol, sodium dioctyl sulfosuccinate or monothioglycerol vitamin E and vitamin E derivatives, such as Vitamin E Tocopherol Polyethylene Glycol 1000 Succinate (TPGS); or other excipients, such as, for example, lauric acid sorbitol ester, triethanol amine oleate or palmitic acid ester and the like. Preferred excipients are complexing agents, such as disodium-EDTA and stabilizers, such as a cyclodextrin and the like. The amount and type of excipient added is in accordance with the particular requirements and is generally in the range of from approximately 0.0001% by weight to approximately 90% by weight.

In another embodiment of the present invention, the ophthalmic composition includes a therapeutically effective amount of an imidazoline such as phentolamine, a carrier, a solubilizer and another therapeutically effective pharmaceutical agent which may be, for example, an anti-redness agent such as tetrahydrazolene, an antibiotic, an antiallergic, an anesthetic, or another drug.

A range of different active agents such as imidazolines are known to those skilled in the art. The present invention is intended to encompass such compounds and equivalent compounds which have substantially the same therapeutic effect. Specifically, the present invention is intended to encompass formulations which include an aqueous solvent having dissolved therein a therapeutically effective amount of a compound which compound when dissolved in the formulation in a low concentration, such as 10% or less, even as low as 1% or less, and administered to a human patient's eye will prevent dilation of the eye in dim light to a level which is about two to five times in diameter the amount of dilation or less than occurs when the patient is present in bright light.

Bioflavonoids, known to reduce capillary permeability, and demulcents, known to protect mucous membranes, may be used in conjunction with an alpha 1 antagonist to reduce vascular permeability increase.

In an embodiment, the formulations of the present invention further promote corneal absorption over vascular effect via a chemical modulation of a vascular tissue. The chemical modulation provides a temporary shielding or binding to a conjunctiva of the eye, wherein the chemical modulation increases corneal absorption without effect on vascular absorption or while decreasing vascular absorption. The chemical modulation occurs through exposure to one or more substances, such as a bioflavonoid, vitamin A, and substances derived from fruits and vegetables in order to reduce capillary permeability, including herbal extracts including aescin. In an embodiment, the chemical modulation occurs through a chemical modulator, such as an azone, a collagen corneal shield, a cyclodextrin including a charged cyclodextrin and a sulfated cyclodextrin, a bioadhesive polymer, a microsphere, a chitosan, a captisol and derivatives. In an embodiment, the chemical absorption is increased via one or more carrier particles, such as nanoparticles including liposomes and emulsions, dendrimers, buckeyballs and the like.

Artificial Tears

As indicated above a simple formulation of the present invention according to an embodiment includes an aqueous solvent which may be sterile water suitable for administration to the eye having an active agent, such as an imidazoline, an alpha selective antagonist, and the like, dissolved therein in a low concentration, e.g., 10% concentration or less as discussed above. However, preferred formulations of the present invention include the active agent dissolved in a formulation which is referred to in the art as an artificial tear formulation. Such artificial tear formulations are disclosed and described within U.S. Pat. Nos. 5,895,645; 5,627,611; and 5,591,426 as well as patents and publications cited and referred to in these patents, all of which are intended to be incorporated herein by reference.

Artificial tear formulations of the present invention in an embodiment promote good wettability and spread. Further, the artificial tear formulations preferably have good retention and stability on the eye and do not cause significant discomfort to the user. A preferred artificial tear composition of the present invention, in an embodiment, includes (1) polyvinylpyrrolidone, preferably in the amount of about 0.1 to 5% by weight of said solution;

(2) benzalkonium chloride, preferably in an amount of about 0.01% to about 0.10% by weight;

(3) hydroxypropyl methylcellulose, preferably in an amount of about 0.2% to about 1.5% by weight of said solution; and (4) glycerin, preferably in an amount of about 0.2% to about 1.0% by weight of said solution, wherein the composition is an aqueous solution having isotonic properties.

Those skilled in the art will recognize that a wide range of different formulations and artificial tear formulations which can be utilized in connection with the present invention.

Eyedroppers

Formulations of the present invention can be administered in a manner generally known to those skilled in the art. In an embodiment, the formulation is administered using an eyedropper. The eyedropper can be constructed in any suitable way. For example, the eyedropper apparatus 10 includes an eyedropper part 12 which includes a hollow cylindrical barrel 14 having a first end 16 and a second end 18 and an inner surface as shown in FIG. 1. Further, the eyedropper 12 includes means for providing suction to draw the formulation of the invention into the hollow cylindrical barrel. For example, the eyedropper part 12 includes a suction device 20 that includes a suction member 22 attached to the first end 16 of the cylindrical barrel 14 such that liquid can be drawn into and out of the cylindrical barrel 14. The suction member 22 can be made from any suitable material, such as a rubber material, or other suitable material that is not reactive with the ophthalmic formulation. The suction member 22 optionally includes an attachment part 24 that allows the eyedropper part to be attached to a container 26 holding the formulation 28 in any suitable way. In this regard, the eyedropper part can be attached to the container after use, thus allowing storage of the formulation within a closed system. The first end 16 of the barrel 14 is configured to receive the means for providing suction to draw in a formulation. The second end 18 of the barrel is generally configured to have a small opening 30 which permits passage of the formulation and allows drops of the formulation to be metered out directly onto the patient's eye. The cylindrical barrel 14 is preferably designed so that it is relatively small and contains less than about 5 cubic centimeters of formulation and may be calibrated to allow for ease of measurement if desired.

It may be desirable to utilize a measured dose eyedropper of the type described within U.S. Pat. No. 5,514,118 or an illuminated eyedropper device of the type described in U.S. Pat. No. 5,584,823. A range of other eye droppers can also be utilized of the type described within the following U.S. Pat. Nos. 5,059,188; 4,834,727; 4,629,456; and 4,515,295. The patents cited here which disclose eyedroppers are incorporated herein by reference as are the various patents and publications cited and discussed within these patents.

Figure 2:
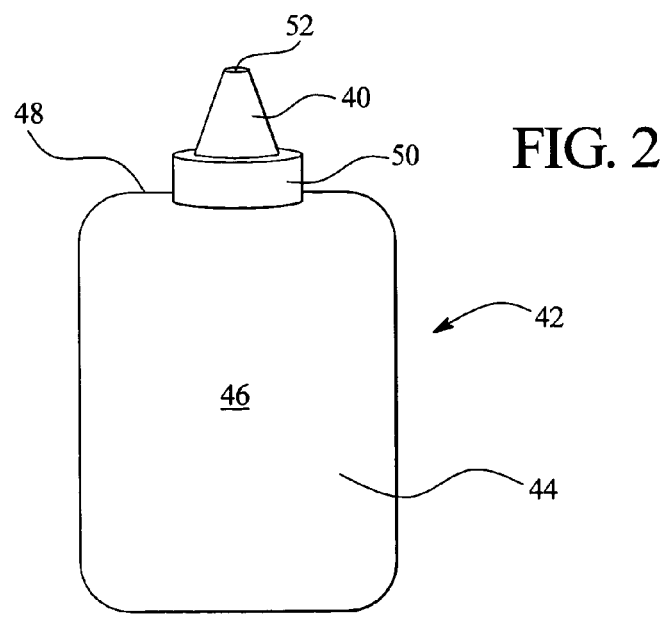
FIG. 2 schematically illustrates an eyedropper apparatus according to another embodiment of the present invention.

The eyedropper apparatus can be configured in any suitable manner as previously discussed. An alternative embodiment is shown in FIG. 2 where the eyedropper part 40 is an integral part of the apparatus 42 and thus is not removably attachable from the apparatus 42 such as the eyedropper part discussed above. As shown in FIG. 2, the eyedropper apparatus 42 includes a reservoir 44 that can hold or contain the formulation 46. The reservoir 44 includes an end 48 in which the eyedropper part 40 is attached thereto. For example, the eyedropper 42 can include an attachment member 50 positioned between the eyedropper part 40 and the reservoir 44. This can be utilized to accept a cap (not shown) or other similar part in order to close the apparatus after use. The eyedropper part has an opening 52 through which the formulation can be administered to the patient.

Examples of the present invention are provided below according to an embodiment without limitation.

EXAMPLE 1

A 5 mg/ml vial of phentolamine was diluted in an artificial tear formulation to approximately 6.0 cc of solution. The artificial solution created an effective composition for reducing the pupillary diameter in reduced light via topical instillation as an eye drop. This method induces mild conjunctival and episcleral blood vessels causing very slight, transient redness to the eye.

EXAMPLE 2

The composition of Example 1 is applied as a single drop to a moist soft contact lens with no excess saline, and the medication is delivered topically over an optional 15 minute to 2 hour period, 30 minutes preferred, through wear of the soft contact lens after which time it is removed. This greatly reduces any systemic absorption of the medication and vasodilation of the vessels, and minimizes redness as a result, while allowing efficient drop utilization with the most effective concentrations to reach the iris dilator muscles and minimize dilation in scotopic conditions. The loss of muscle tone of these muscles may result in constriction of the pupil, but not sufficient to cause the dimness from a pinpoint pupil effect commonly seen with acetylcholine or cholinesterase inhibitors. Phentolamine has the advantage of creating a longer lasting effect chemical sympathectomy, reducing the frequency of application required to maintain effective scotopic viewing.

Phentolamine as modified and applied requires a single instillation per day to render up to 20 to 24 hours of effect. Phenoxybenzamine formulations ranging from 0.1% to 5% have not been as effective as phentolamine, and induce much more vasodilation and congestion. Similarly, prazosin and tolamine at 0.1% to 5% exhibits slight pupillary reduction in dilation in dim light but appears to be less effective than phentolamine. Labetalol, a potent beta adrenergic receptor antagonist, consists of four isomers, two of which have some alpha 1 antagonist activity. Its S,S and S,R isomers, and in concentrations of 0.1% to 2%, 0.5% preferred, are modestly effective. Other alpha 1 antagonists such as tamsulosin, bunazosin, alfuzonsin, urapidil, ketanserin, and indoramin, in concentrations of 0.1% to 2%, with 0.5% preferred are believed to provide clinical effectiveness as well. In particular, it is believed that alpha 1a selective antagonists, such as tamsulosin, urapidil and the like, can effectively act as a sole active agent to optimize pupil light reflex in reduced light while minimizing redness as previously discussed. Alpha-2 receptor antagonists, such as found in Yohimbe extract, do not appear to have an effect on pupil dilation in reduced light.

Neuroleptic agents such as chlorpromazine, and ergot alkaloids such as ergotamine have mild alpha 1 receptor antagonist activity and may exhibit mild effectiveness for the purposes of the present invention.

TABLE 1

Effect of Alpha Adrenergic Receptor Antagonists on Pupil Dilation

| Compound | Adrenergic receptors blocked | Effect on pupil diam. in darkness (mm) | Redness (direct topical instillation) | Duration (hrs) | Concentration |
| --- | --- | --- | --- | --- | --- |
| Phentolamine | a-1 | 7.5 -> 4.0 | + | 20-40 | 3.3 mg/ml* |
| Phenoxybenzamine | a-1 | 7.5 -> 5.5 | ++++ | ≥20 | 5 mg/ml |
| Prazosin | a-1, 2 | 7.5 -> 6 | +++ | 5-12 | 5 mg/ml |
| Dapiprazole | a-1, 2 | 7.5 -> 7 | +++ | 5-12 | 5 mg/ml |
| Yohimbe | a-2 | 7.5 -> 7.5 | + | 0 | 5 mg/ml |
| Tolamine | a-1 | 7.5 -> 6 | + | 5-12 | 5 mg/ml |

*applied via soft contact lens with 1-2 gtts applied and placed for 30 minutes before removed

TABLE 2

Effect of Phentolamine 0.35% on Pupil Diameter**

| Subject | Dim Light Pre mm | Bright Light Pre mm | Dim Light Post mm | Bright Light Post mm | Comments |
|---|---|---|---|---|---|
| NF | 7.0 | 3.5 | 4.0 | 3.0 | Night vision good pre and post |
| NB | 7.5 | 4.0 | 4.0 | 3.0 | Had glare, halos, poor night vision pre: post night = day = exc; glare = 0; halos 70% reduced; depth perception improved |
| LR | 7.5 | 3.0 | 4.0 | 2.5 | Had glare, halo's poor night vision pre: post night much improved, dim light about same. |
| GH | 3.5 | 3.0 | 3.0 | 2.5 | Night vision good pre and post |
| LH | 4.0 | 3.0 | 3.5 | 2.5 | Night vision good pre and post |

Phentolamine 3.3 mg/cc applied as a single drop to a soft contact lens placed for 30 minutes. Application of drops morning or daytime.

As shown below, Table 3 demonstrates the results of administering phentolamine eye drops, an alpha adrenergic antagonist, to several patients pursuant to an embodiment of the present invention. The results illustrate the benefit that is derived from reducing pupil diameter by 1 mm or more and/or pupil area by 20% or more in dim light conditions pursuant to an embodiment. In this regard, a significant increase in spherical aberrations is typically found per each one millimeter of increase in pupil size diameter above 5 mm. These aberrations generally increase as a function of severity of the refractive error, particularly increases in the myopic spherical equivalent of refractive error. Coma may increase, as well as other higher order aberrations, as pupil size diameter increases, again especially as refractive error increases. Thus, a reduction in pupil diameter by 1 mm or more and/or pupil area by 20% or more can effectively act to improve vision in dim light conditions. As previously discussed, the present invention contemplates the use of a single active agent, preferably an alpha 1a selective antagonist, that can optimize pupil light reflex while minimizing, if not eliminating, redness.

TABLE 3

Effect of Phentolamine on Visual Acuity in Dim Light

| | Pupil Diameter in Dim Light | | Pupil Diameter | Pupil | Dim Light Contrast | |
|---|---|---|---|---|---|---|
| Subject No. | Pre-Drug mm | Post-Drug mm | Change mm | Area Change % | Pre-Drug | Post-Drug |
| 1 | 8.2 | 7.4 | 0.8 | 19% | 20/40 | 20/32 |
| 2 | 7.8 | 5.9 | 1.9 | 43% | 20/53 | 20/50 |
| 3 | 7.7 | 6.9 | 0.8 | 20% | 20/29 | 20/25 |
| 4 | 8.5 | 7.1 | 1.4 | 30% | 20/29 | 20/22 |
| 5 | 7.9 | 5.9 | 2.0 | 44% | 20/35 | 20/20 |
| 6 | 7.8 | 6.9 | 0.9 | 22% | 20/32 | 20/24 |
| 7 | 7.9 | 7.5 | 0.4 | 10% | 20/63 | 20/38 |
| 8 | 8.2 | 7.1 | 1.1 | 25% | 20/38 | 20/21 |
| 9 | 7.9 | 6.5 | 1.4 | 32% | 20/32 | 20/21 |

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a compound" includes a plurality of such compounds and reference to "the step" includes reference to one or more steps and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All of the references cited herein are incorporated by reference in their entirety.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method of modulating pupil dilation, the method comprising: administering to an eye of an individual an ophthalmic formulation in an emulsified form comprising a sterile aqueous carrier including an ophthalmic artificial tear solution, and a therapeutically effective amount of an alpha 1 antagonist that selectively effects an iris alpha adrenergic receptor over a vascular alpha adrenergic receptor; and allowing the ophthalmic formulation to remain in contact with the eye for a period of time in a reduced light where a dilator muscle of the eye receives greater stimulation in absence of the ophthalmic formulation and eye redness is minimized, wherein the alpha 1 antagonist comprises a dihydroindole, and wherein the dihhydroindole is KMD-3213.

2. The method of claim 1, wherein the ophthalmic formulation is administered in an amount so as to provide an optimized pupil diameter of about 6 mm or less.

3. The method of claim 2, wherein the optimized pupil diameter ranges from about 3 mm to about 5 mm.

4. The method of claim 2, wherein the optimized pupil diameter ranges from about 2.75 mm to about 4 mm.

5. The method of claim 1, wherein the ophthalmic formulation does not effect a pupil diameter at about 2 mm or less in a bright light.

6. The method of claim 1, wherein a pupil diameter is reduced by about 1 mm or more to optimize pupil diameter.

7. The method of claim 1, wherein a pupil area is reduced by about 20% or more to optimize pupil diameter.

8. The method of claim 1, wherein the ophthalmic formulation is administered in an amount so as to reduce an adverse visual effect.

9. The method of claim 8, wherein the adverse visual effect is due to at least one of a perceived light scattering, a reduced contrast sensitivity and a reduced acuity.

10. The method of claim 9, wherein the adverse visual effect is due to an imperfect aspheric peripheral corneal curvature.

11. The method of claim 9, wherein the adverse visual effect is due to a higher order aberration of the eye selected from the group consisting of a coma, a secondary astigmatism, a spherical aberration, a trifoil, quadrafoil, and a tetrafoil.

12. The method of claim 9, wherein the adverse visual effect is due to an uncorrected spherocylindrical correction contributed to by peripheral zones of a cornea.

13. A method of administering an ophthalmic formulation comprising a sterile aqueous carrier including an ophthalmic artificial tear solution to an eye of an individual comprising administering a therapeutically effective amount of an alpha 1 antaonist within the ophthalmic formulation that selectively effects an iris alpha adrenergic receptor over a vascular alpha adrenergic receptor wherein the ophthalmic formulation optimizes a pupil diameter while effectively minimizing eye redness, wherein the alpha 1 antagonist comprises dihydroindole, and wherein the dihydroindole is KMD-3213.

14. The method of claim 13, wherein the ophthalmic formulation further promotes conical absorption over vascular effect via a chemical modulation of a vascular tissue.

15. The method of claim 14, wherein the chemical modulation includes a temporary shielding or binding to a conjunctiva of the eye.

16. The method of claim 14, wherein the chemical modulation increases corneal absorption without effect on vascular absorption.

17. The method of claim 14, wherein the chemical modulation increases corneal absorption while decreasing vascular absorption.

18. The method of claim 14, wherein the chemical modulation occurs through exposure to one or more substances selected from the group consisting of a bioflavonoid, vitamin A, and substances derived from fruits and vegetables in order to reduce capillary permeability, including herbal extracts including aescin.

19. The method of claim 14, wherein the chemical modulation occurs through use of one or more substances selected from the group consisting of demulcents, herbal extracts, horse chestnut extracts, and a substance containing mucilage.

20. The method of claim 13, wherein a mucous membrane of the eye is protected from chemical irritants, to soothe the eye and/or to reduce redness, burning, stinging, or dryness by binding a protective layer to the mucous membrane of the eye and the conjunctiva.

21. The method of claim 13, wherein a mucous membrane of the eye is protected from chemical irritants, to soothe the eye and/or to reduce redness, burning, stinging, or dryness by reducing a capillary permeability of the eye and increasing a venous tone by using bioflavonoids.

22. The method of claim 14, wherein the chemical modulation occurs through a chemical modulator selected from the group consisting of an azone, a collagen corneal shield, a cyclodextrin including a charged cyclodextrin and a sulfated cyclodextrin, a bioadhesive polymer, a microsphere, a chitosan, a captisol, and derivatives thereof.

23. The method of claim 14, wherein the chemical absorption is increased via one or more carrier particles selected from the group consisting of nanoparticles including liposomes and emulsions, dendrimers, and buckeyballs.

24. The method of claim 13, wherein the pupil diameter is optimized to about 6 mm or less.

25. The method of claim 24, wherein the pupil diameter is optimized to about 3.0 mm to about 5.0 mm in size.

26. The method of claim 13, wherein the pupil diameter is optimized to about 2.75 mm to about 4.0 mm.

27. The method of claim 13, wherein, the ophthalmic formulation does not effect pupil diameter at about 2 mm or less in a bright light.

28. The method of claim 24, wherein the pupil diameter is reduced by about 1 mm or more to optimize pupil diameter.

29. The method of claim 24, wherein the pupil diameter is optimized by reducing a pupil area by about 20%.

30. The method of claim 13, wherein KMD-3213 acts as a sole active ingredient to optimize pupil diameter.

31. An ophthalmic formulation in an emulsified form for topical administration, the ophthalmic formulation comprising:
a sterile aqueous carrier including an ophthalmic artificial tear solution, and
a therapeutically effective amount of an alpha 1 antagonist that selectively effects an iris alpha adrenergic receptor over a vascular alpha adrenergic receptor for optimizing a pupil diameter in a reduced light while minimizing eye redness,
wherein the alpha 1 antagonist comprises a dihydroindole, and wherein the dihydroindole is KMD-3213.

32. The ophthalmic formulation of claim 31, wherein the alpha 1 antagonist is selective for an iris dilator smooth muscle alpha adrenergic receptor.

33. The ophthalmic formulation of claim 32, wherein the alpha 1 antagonist effectively reduces activity of the iris dilator smooth muscle.

34. The ophthalmic formulation of claim 33, wherein the alpha 1 antagonist reduces activity of the iris dilator muscle effectively without constriction of an iris sphincter muscle.

35. The ophthalmic formulation of claim 31, wherein the alpha 1 antagonist is selective for an alpha 1a adrenergic receptor over an alpha 1b adrenergic receptor.

36. The ophthalmic formulation of claim 31, wherein the ophthalmic formulation is in an eye dropper.

37. The ophthalmic formulation of claim 31, wherein the ophthalmic artificial tear solution includes hydroxypropyl methylcellulose in an amount of about 0.2% to 1.5% by weight of the ophthalmic artificial tear solution.

38. The ophthalmic formulation of claim 31, wherein the pupil diameter is 6 mm or greater.

39. The ophthalmic formulation of claim 31, wherein the pupil diameter is optimized to 6 mm or less.

40. The ophthalmic formulation of claim 31, wherein the pupil diameter is optimized in the reduced light without eye redness.

41. The method of claim 1, wherein the ophthalmic formulation is administered to the eye having a pupil diameter of 6 mm or greater.

42. The method. of claim 1, wherein the ophthalmic formulation is allowed to remain in contact with the eye for the period of time in the reduced light where the dilator muscle of the eye receives greater stimulation in absence of the ophthalmic formulation and without eye redness.

43. The method of claim 13, wherein the ophthalmic formulation optimizes the pupil diameter of 6 mm or greater.

44. The method of claim 13, wherein the ophthalmic formulation optimizes the pupil diameter without eye redness.

* * * * *